(12) United States Patent
Omura et al.

(10) Patent No.: US 7,982,057 B2
(45) Date of Patent: Jul. 19, 2011

(54) COMPOUND OF STEMPHONES AND PRODUCTION THEREOF

(75) Inventors: Satoshi Omura, Tokyo (JP); Hiroshi Tomoda, Tokyo (JP); Rokuro Masuda, Tokyo (JP)

(73) Assignee: The Kitasato Institute, Tokyo (JP)

( * ) Notice: Subject to any disclaimer, the term of this patent is extended or adjusted under 35 U.S.C. 154(b) by 192 days.

(21) Appl. No.: 11/911,868

(22) PCT Filed: Mar. 15, 2006

(86) PCT No.: PCT/JP2006/305625
§ 371 (c)(1),
(2), (4) Date: Dec. 11, 2007

(87) PCT Pub. No.: WO2007/108108
PCT Pub. Date: Sep. 27, 2007

(65) Prior Publication Data
US 2009/0093646 A1    Apr. 9, 2009

(51) Int. Cl.
*C07D 311/78* (2006.01)
(52) U.S. Cl. ...... 549/384; 435/125; 435/170; 435/256.1
(58) Field of Classification Search .................. 549/384; 435/170, 256.1, 125
See application file for complete search history.

(56) References Cited

U.S. PATENT DOCUMENTS
5,879,683 A    3/1999    Hamilton-Miller

FOREIGN PATENT DOCUMENTS
JP    9-509677 A    9/1997

OTHER PUBLICATIONS

Miller, "Experiment 14, Nitrosoguanidine Mutagenesis", Experiments in Molecular Genetics, Cold Spring Harbor: New York, 1972.*
Koyama et al. J. Antibiotics (Nov. 2005) 58(11): 695-703.*
Moubasher, M.H. Bullein of the Faculty of Science, Assiut Univerisity, D; Botany (1999) 28(2): 305-321.*
C. Huber et al., "Stemphone, A New Type of Natural Quinone", Tetrahedron Letters, 1974, vol. 29, pp. 2545-2548.
International Search Report of PCT/JP2006/305625, date of mailing Apr. 18, 2006.

* cited by examiner

*Primary Examiner* — Sandy Saucier
*Assistant Examiner* — Susan Hanley
(74) *Attorney, Agent, or Firm* — Young & Thompson

(57) ABSTRACT

The present invention relates to novel compound of stemphones obtained by culturing microorganism belonging to genus *Aspergillus* and having ability to produce compound of stemphones selected from the group consisting of stemphone D substance, stemphone E substance, stemphone E1 substance, stemphone E2 substance, stemphone E3 substance and stemphone F substance, accumulating the compound of stemphones in the cultured mass, and isolating the compound of stemphones from the cultured mass. Since the obtained compound has enhancing activity for imipenem and activity for reducing cytotoxicity, it can be expected to be useful as lead compounds for combination remedy for methicillin resistant *Staphylococcus aureus* (MRSA) infection.

1 Claim, No Drawings

COMPOUND OF STEMPHONES AND PRODUCTION THEREOF

This application claims priority to PCT/JP2006/305625, filed Mar. 15, 2006, the entire contents of which are hereby incorporated by reference.

TECHNICAL FIELD

The present invention relates to novel compound of stemphones having enhancing effect of β-lactam antibiotic imipenem used as an antibacterial agent in combination with β-lactam antibiotic imipenem, and a process for production thereof.

BACKGROUND ART

Recently, methicillin resistant *Staphylococcus aureus* (hereinafter designates as MRSA) has become a social problem as a major causative microorganism of hospital-acquired infection. This pathogenic microorganism is resistant to various medicines such as β-lactam antibiotic, and antibiotics such as glycopeptide antibiotic vancomycin and aminoglycoside antibiotic arbekacin, which are reported at present to exhibit almost no resistance, are generally used for treatment of MRSA. In addition to this, combination therapy of β-lactam antibiotics or that of β-lactam antibiotic and other antibiotic having different active site is employed at present (Yoshimi Hasegawa et al. "Science of antibiotic administration", p. 264-273, 1998).

PRIOR ART

Resistant strains against vancomycin and arbekacin have already appeared. It has become a problem that these antibiotics have been known to have adverse reaction to exhibit hearing impairment caused by eight cranial nerve disorder. In order to cope with these problems, a substance having an action for recovering effect of β-lactam antibiotic has been reported to date. For example, tea extract or active fraction thereof showing synergistic effect by using in combination with antimicrobial agent including β-lactam antibiotic are agree with that (JP-A-9-509677).

DISCLOSURE OF THE INVENTION

Novel stemphones are clearly distinguished from the polyphenol compounds, which are the active ingredients of the tea extract or the active fraction thereof, in their molecular formulae and chemical structures. Further, the present inventors have already reported two types of imipenem activating substance named as stemphone B substance and stemphone C substance isolated from cultured liquid of fungal strain FKI-2136. Especially, since stemphone C substance has enhancing action to give 512-fold activity of MIC of imipenem from 16 μg/ml to 0.03 16 μg/ml, furthermore it has enhancing action to give 512- and 16-fold activity of MIC of cloxacillin and cefazolin, respectively, application for combination drug with β-lactam antibiotic against methicillin resistant *Staphylococcus aureus* (hereinafter designates as MRSA) will be expected.

It is expected that medicament enhancing activity of β-lactam antibiotic may reduce frequency of emergence of resistant bacteria by decreasing dosage of β-lactam antibiotic and shorten dosing period. It is also expected at the same time that resistance against β-lactam antibiotic may be overcome by combining two medicaments having different mode of action.

Under such circumstance, an object of the present invention is to provide the substance having enhancing activity of β-lactam antibiotic against MRSA, and it will be useful as the novel remedy for infectious diseases of MRSA and infectious diseases caused by multi-drug resistant bacteria including β-lactam antibiotic resistance.

The present inventors have explored completely a cultured liquid of fungal strain FKI-2136 previously isolated from soil, and found that substance having enhancing activity of imipenem different from stemphone B substance and stemphone C substance was produced. Subsequently, three types of substance having activity with enhancing action for imipenem were isolated and purified. Since substances having such chemical structures have not been known, the substances were designated as stemphone D substance, stemphone E substance and stemphone F substance. In addition, with regard to stemphone E substance, as a result of preparing derivatives thereof, since substances having such chemical structures have not been known, the substances were designated as stemphone E1 substance, stemphone E2 substance and stemphone E3 substance.

The present invention has completed based on such knowledge, and an aspect of the present invention is to provide compound of stemphones, as described in claim 1, selected from the group consisting of stemphone D substance represented by the following formula [I],

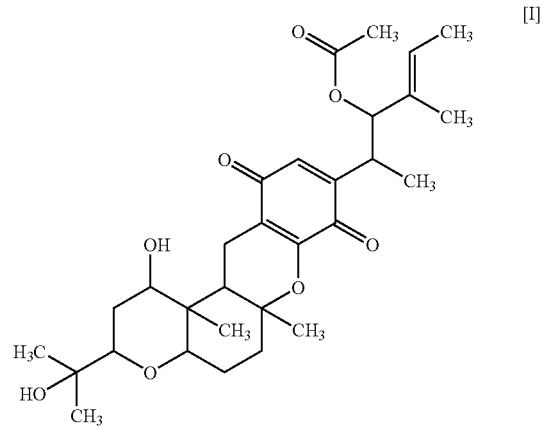

stemphone E substance represented by the following formula [II],

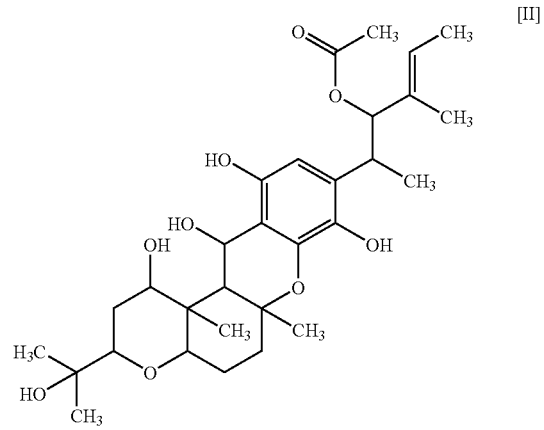

stemphone E1 substance represented by the following formula [III],

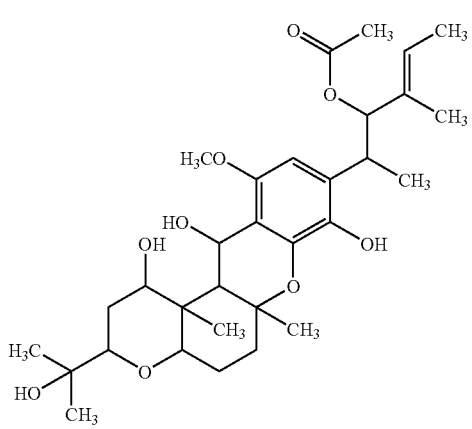

stemphone E2 substance represented by the following formula [IV],

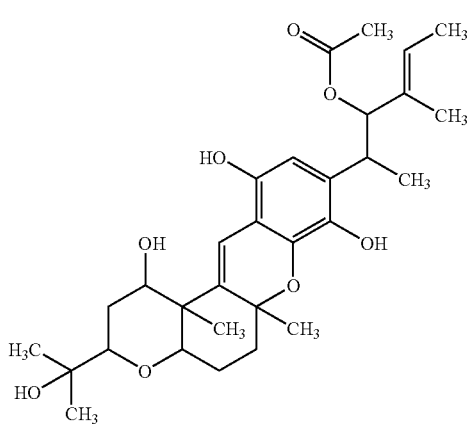

stemphone E3 substance represented by the following formula [V],

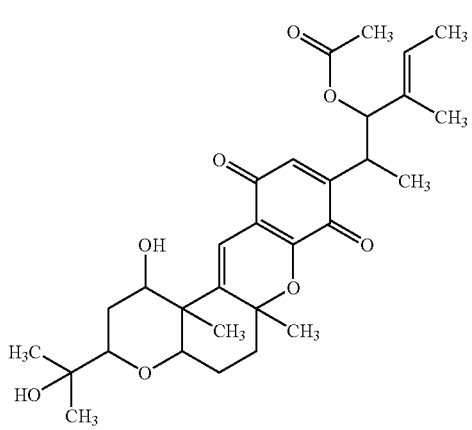

and stemphone F substance represented by the following formula [VI].

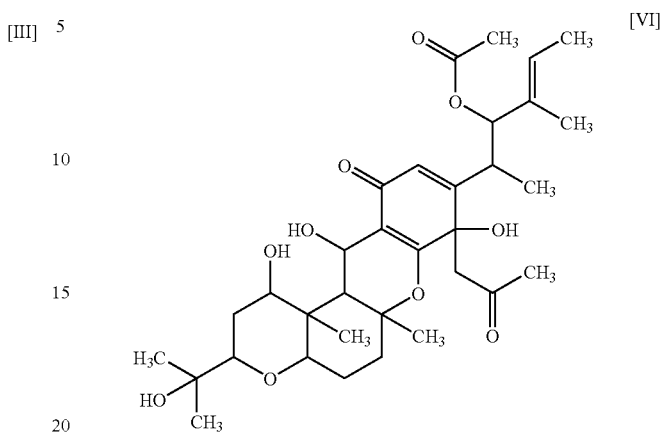

Another aspect of the present invention is to provide a process for production of stemphones comprising culturing a microorganism belonging to genus *Aspergillus* and having ability to produce compound of stemphones as described in claim 1 selected from the group consisting of stemphone D substance, stemphone E substance, stemphone E1 substance, stemphone E2 substance, stemphone E3 substance, and stemphone F substance, accumulating stemphones in a cultured mass and isolating stemphones from the cultured mass.

Further aspect of the present invention is to provide such that a microorganism belonging to genus *Aspergillus* and having ability to produce stemphones is *Aspergillus* sp. FKI-2136 NITE BP-83.

Further aspect of the present invention is to provide *Aspergillus* sp. FKI-2136 NITE BP-83.

An example of the microorganism strain used for producing novel compound of stemphones represented by the formula [I], [II], [III], [IV], [V] and [VI] (hereinafter designates as "FKI-2136 substance producing strain") is *Aspergillus* sp. FKI-2136 strain newly isolated from soil of Ishigaki-jima, Okinawa Pref. by the present inventors. Culturing properties of the strain are as follows.

Morphological Properties

The strain shows good growth on Czapeck yeast extract agar medium, malt extract agar medium and Czapeck yeast extract added with 20% sucrose agar medium, and good bearing conidiospore is observed.

When colonies grown on Czapeck yeast extract agar medium are observed microscopically, hyphae are colorless and have septa. Conidiophores are directly grown from substrate mycelia and length is 175-730 µm with inverted T-form foot cells. A tip of the conidiophore becomes hypertrophied from globose to subglobose with forming vesicle with a diameter 15-60 µm. Aspergilla are biseriate and consisting of metulae (6-12×3-6 µm) and ampullar phialide (5-10×2-3 µm). Vesicle is covered almost all Aspergilla. Conidium is formed from a top of phialide, and grows to chain-like form depending upon culturing period. Conidium is globose to subglobose, pale orcher, sized 2-4 µm with smooth surface.

Culturing Properties

Results of macroscopic observation of the strain cultured on various agar media a 25° C. for 7 days are shown hereinbelow.

| Medium Growth condition on medium (diameter of colony) | Color of surface of colony | Color of reverse of colony | Soluble pigment |
|---|---|---|---|
| Czapeck yeast extract agar medium | | | |
| Good (60-65 mm) Flocky - velvety Wavy Smooth edge | white-cream | grayish-yellow | None |
| Malt extract agar medium | | | |
| Good (60-65 mm) Flocky - velvety Smooth edge | cream-pale ocher | gray | None |
| 20% sucrose Czapeck yeast extract agar medium | | | |
| Good (65-70 mm) Flocky - velvety Wavy Smooth edge | white-cream | cream-grayish yellow | None |

In addition, although the strain was cultured on Czapeck yeast extract agar medium at 5° C. and 37° C. for 14 days, no growth was observed.

Physiological Properties
1) Optimum Growth Condition
    Optimum growth condition of the strain is pH 4-8 at 11.5-29° C.
2) Growth Range
    Growth range of the strain is pH 3-10 at 10-30.5° C.
3) Nature for Growth Condition: Aerobic International Deposition of Microorganism Based on the morphological properties, culturing characteristics and physiological properties of the above FKI-2136 strain, as a result of comparison with known microbial species, the strain is identified as the strain belonging to genus *Aspergillus* and designated as *Aspergillus* sp. FKI-2136. The strain *Aspergillus* sp. FKI-2136 was deposited, according to the Budapest Treaty on the International Recognition of the Deposit of Microorganisms for the Purposes of Patent Procedure, in Independent Administrative Agency National Institute of Technology and Evaluation NITE Patent Microorganisms Depositary (NPMD), 2-5-8, Kazusakamatari, Kisarazu-shi, Chiba-ken, 292-0818 Japan. Date of deposit is Mar. 3, 2005 and accession number is NITE BP-83.

With regard to FKI-2136 substance producing microorganism strain used in the present invention, the strain *Aspergillus* sp. FKI-2136 hereinbefore can be mentioned as a preferable example. However, it is well known that the microorganism is very easily mutated in the general mycological properties and can not be maintained constant in the mycological properties, and is mutated by natural means or artificial means, for example commonly used ultraviolet irradiation or mutation inducer such as N-methyl-N'-nitro-N-nitrosoguanidine and 2-aminopurine. Consequently, the strains belonging to genus *Aspergillus* and having ability to produce compound of stemphones represented by the formula [I], [II], [III], [IV], [V] and [VI], including artificial mutants and natural mutants, can be used in the present invention.

The production of stemphones of the present invention can be performed at first by culturing FKI-2136 substance producing microorganism. As for nutrient sources preferable for production of the compound of stemphones, carbon sources which can be assimilable by microorganism, nitrogen sources which can be digestible, and if necessary nutrient medium containing inorganic salt, vitamin, etc. can be used. Examples of assimilable carbon sources are sugars such as glucose, fructose, maltose, lactose, galactose, dextrin and starch, and vegetable oil such as soybean oil. These are used alone or in combination.

Examples of digestible nitrogen sources are peptone, yeast extract, meat extract, soybean powder, cotton seed powder, corn steep liquor, malt extract, casein, amino acids, urea, ammonium salts and nitrate. These are used alone or in combination. If necessary, salts such as phosphate, magnesium salt, calcium salt, sodium salt and potassium salt, heavy metal salt such as iron salt, manganese salt, copper salt, cobalt salt and zinc salt, vitamins and substances preferable for stemphones production can be added.

In the culture, when forming occurs heavily, if necessary, antifoaming agent such as liquid paraffin, animal oil, vegetable oil, silicone oil and surface active agent can be added. The culture can be performed by liquid culture or solid culture, if above nutrient sources are contained. In general, the liquid medium may conveniently used for the culture. In case of small culture, the culture using flask is preferable. In case of industrial mass production of the objective substance, stirring aeration culture may be preferable as like in the other fermentation products.

In the large scale production using tank culture, in order to prevent growth delay of the microorganism in the production process, it is preferable that the production strain is at first inoculated and cultured in the relatively small amount of medium, and the cultured mass is transferred into the large tank and is continued to culture. In this case, composition of the medium used in the pre-cultivation and the medium used in the production culture can be same or if necessary it can be different.

When the culture is performed in aeration with stirring, known method such as stirring by propeller and other mechanical stirring, rotary or shaking the fermenter, pumping or bubbling aeration can be applied. Sterilized air is used for aeration.

Culturing temperature can be changed within ranges for production of the compound of stemphones by the FKA-25 substance producing strain, generally at 20-30° C., preferably around at 27° C. Culturing pH is generally 5-8, preferable around 7. Culturing time depends on the culturing condition and is generally 4-7 days. The compound of stemphones accumulated in the thus obtained cultured mass is generally found in the cultured mycelia and cultured liquid. In order to collect the compound of stemphones from the cultured mass, total cultured mass is subjected to extraction with water miscible organic solvent such as acetone, subsequently the organic solvent is removed in vacuo from the extracted liquid, then the residue is extracted with water immiscible organic solvent such as ethyl acetate.

In addition to the above mentioned extraction methods, known methods used for collecting lipophilic substance, for example, adsorption chromatography, gel filtration chromatography, centrifugal countercurrent distribution chromatography, high performance liquid chromatography, etc. can be used alone or in combination, or repeatedly, thereby isolating and purifying the compound of stemphones.

Physico-Chemical Properties

Physico-chemical properties of the compound of stemphones of the present invention are explained.

Stemphone D Substance
(1) Property: yellow powder
(2) Molecular formula: $C_{30}H_{42}O_8$
    HRFAB-MS (m/z) [M+Na]$^+$ Calculated value: 553.2777, Measured value: 553.2788
(3) Molecular weight: 530
    FAB-MS (m/z) [M+H]$^+$ 531

(4) Ultraviolet absorption spectrum: UV spectrum measured in methanol solution. λmax (MeOH, ε): Absorption at 203 nm (17442), 265 nm (8284), 396 nm (678)

(5) Infrared absorption spectrum: IR spectrum measured by KBr tablet. Characteristic absorption maximum: vmax at 3442, 2973, 1735, 1643, 1604 $cm^{-1}$, etc.

(6) Specific rotation: $[\alpha]_D^{26}$ +93.0° (c=0.1, methanol)

(7) Solubility in solvent: Soluble in methanol and chloroform, and insoluble in water.

(8) Proton and carbon nuclear magnetic resonance spectra: Chemical shift of hydrogen (ppm) and that of carbon (ppm) measured in deuterated chloroform by using Varian 300 MHz NMR spectrometer are as shown hereinbelow.

$\delta_H$: 0.89 (3H), 1.02 (3H), 1.15 (3H), 1.20 (3H), 1.29 (3H), 1.48 (1H), 1.60 (4H), 1.61 (3H), 1.82 (2H), 1.94 (3H), 2.00 (1H), 2.12 (2H), 2.15 (1H), 2.50 (1H), 3.34 (1H), 3.58 (1H), 3.70 (1H), 3.90 (1H), 5.14 (1H), 5.55 (1H), 6.48 (1H) ppm $\delta_H$: 11.6, 12.8, 13.1, 16.1, 17.1, 20.9, 21.1, 23.8, 24.9, 26.2, 29.9, 33.4, 36.7, 38.9, 39.7, 69.3, 71.8, 75.9, 78.9, 81.0, 81.6, 117.7, 125.0, 132.0, 132.4, 148.0, 152.4, 169.9, 181.3, 187.1 ppm As explained hereinabove, as a result of detailed examination on various physico-chemical properties and spectral data of stemphone D, stemphone D substance was determined to have chemical structure represented by the formula [I].

Stemphone E Substance (1) Property: white powder (2) Molecular formula: $C_{30}H_{44}O_9$
HRFAB-MS (m/z) [M+H]$^+$ Calculated value: 549.2986, Measured value: 549.2977

(3) Molecular weight: 548
FAB-MS (m/z) [M+H]$^+$ 549

(4) Ultraviolet absorption spectrum: UV spectrum measured in methanol solution. λmax (MeOH, ε): Absorption at 204 nm (34447), 292 nm (4370), 356 nm (403)

(5) Infrared absorption spectrum: IR spectrum measured by KBr tablet. Characteristic absorption maximum: vmax at 3434, 2929, 1718, 1629 $cm^{-1}$, etc.

(6) Specific rotation: $[\alpha]_D^{26}$ +100.8° (c=0.1, methanol)

(7) Solubility in solvent: Soluble in methanol and chloroform, and insoluble in water.

(8) Proton and carbon nuclear magnetic resonance spectra: Chemical shift of hydrogen (ppm) and that of carbon (ppm) measured in deuterated chloroform by using Varian 300 MHz NMR spectrometer are as shown hereinbelow.

$\delta_H$: 0.97 (3H), 0.99 (3H), 1.13 (3H), 1.18 (3H), 1.24 (3H), 1.58 (1H), 1.60 (1H), 1.62 (3H), 1.64 (3H), 1.78 (3H), 1.80 (1H), 1.88-1.92 (3H), 2.32 (1H), 3.44 (1H), 3.58 (1H), 3.70 (1H), 4.14 (1H), 5.06 (1H), 5.34 (1H), 5.63 (1H), 6.18 (1H) ppm $\delta_c$: 10.9, 12.9, 13.1, 17.6, 21.2, 22.1, 23.7, 25.1, 26.0, 28.1, 33.8, 37.6, 40.5, 46.5, 63.6, 70.7, 72.0, 76.6, 79.5, 80.4, 83.1, 104.6, 111.0, 125.8, 128.8, 132.5, 136.5, 139.7, 147.4, 171.4 ppm As explained hereinabove, as a result of detailed examination on various physico-chemical properties and spectral data of stemphone E, stemphone E substance was determined to have chemical structure represented by the formula [II].

Stemphone E1 Substance (1) Property: white powder (2) Molecular formula: $C_{31}H_{46}O_9$
HRFAB-MS (m/z) [M+H]$^+$ Calculated value: 563.3142, Measured value: 563.3153

(3) Molecular weight: 562
FAB-MS (m/z) [M−H]$^-$ 561

(4) Ultraviolet absorption spectrum: UV spectrum measured in methanol solution. λmax (MeOH, ε): Absorption at 202 nm (34503), 291 nm (3889), 360 nm (422)

(5) Infrared absorption spectrum: IR spectrum measured by KBr tablet. Characteristic absorption maximum: vmax at 3432, 2931, 1727, 1633 $cm^{-1}$, etc.

(6) Specific rotation: $[\alpha]_D^{26}$ +97.0° (c=0.1, methanol)

(7) Solubility in solvent: Soluble in methanol and chloroform, and insoluble in water.

(8) Proton and carbon nuclear magnetic resonance spectra: Chemical shift of hydrogen (ppm) and that of carbon (ppm) measured in deuterated chloroform by using Varian 300 MHz NMR spectrometer are as shown hereinbelow.

$\delta_H$: 1.00 (3H), 1.08 (3H), 1.15 (3H), 1.21 (3H), 1.25 (3H), 1.50-1.60 (2H), 1.64 (3H), 1.67 (3H), 1.80 (3H), 1.81 (1H), 1.88-2.06 (3H), 2.35 (1H), 3.43 (1H), 3.60 (1H), 3.74 (1H), 3.82 (3H), 4.12 (1H), 5.06 (1H), 5.21 (H), 5.45 (1H), 5.67 (1H), 6.27 (1H) ppm $\delta_c$: 11.3, 13.3, 13.4, 17.6, 21.4, 22.3, 23.9, 25.4, 26.6, 28.4, 34.0, 37.8, 40.8, 46.9, 55.7, 63.5, 71.0, 72.0, 77.3, 79.7, 80.9, 82.5, 101.2, 112.2, 125.6, 128.6, 132.9, 137.9, 140.1, 150.3, 170.4 ppm As explained hereinabove, as a result of detailed examination on various physico-chemical properties and spectral data of stemphone E1, stemphone E1 substance was determined to have chemical structure represented by the formula [III].

Stemphone E2 Substance (1) Property: white powder (2) Molecular formula: $C_{30}H_{42}O_8$
HRFAB-MS (m/z) [M+H]$^+$ Calculated value: 531.2980, Measured value: 531.2896

(3) Molecular weight: 530
FAB-MS (m/z) [M−H]$^-$ 529

(4) Ultraviolet absorption spectrum: UV spectrum measured in methanol solution. λmax (MeOH, ε): Absorption at 202 nm (33533), 287 nm (21722)

(5) Infrared absorption spectrum: IR spectrum measured by KBr tablet. Characteristic absorption maximum: vmax at 3434, 2975, 1720, 1637 $cm^{-1}$, etc.

(6) Specific rotation: $[\alpha]_D^{26}$ +200.5° (c=0.1, methanol)

(7) Solubility in solvent: Soluble in methanol and chloroform, and insoluble in water.

(8) Proton and carbon nuclear magnetic resonance spectra: Chemical shift of hydrogen (ppm) and that of carbon (ppm) measured in deuterated chloroform by using Varian 300 MHz NMR spectrometer are as shown hereinbelow.

$\delta_H$: 1.04 (3H), 1.13 (3H), 1.18 (3H), 1.22 (3H), 1.42 (3H), 1.64 (3H), 1.67 (3H), 1.70 (2H), 1.81 (3H), 1.82 (1H), 1.96 (1H), 2.01 (1H), 2.12 (2H), 3.45 (1H), 3.64 (1H), 3.86 (1H), 4.28 (1H), 5.41 (1H), 5.66 (1H), 6.22 (1H), 6.60 (1H) ppm $\delta_c$: 11.0, 13.2, 17.6, 20.5, 21.3, 23.8, 24.0, 26.3, 26.6, 27.9, 34.6, 37.1, 44.3, 69.3, 71.9, 74.5, 77.9, 78.9, 82.8, 105.9, 108.8, 113.7, 125.7, 130.0, 132.5, 136.6, 138.3, 139.5, 144.2, 170.9 ppm As explained hereinabove, as a result of detailed examination on various physlco-chemical properties and spectral data of stemphone E2, stemphone E2 substance was determined to have chemical structure represented by the formula [IV].

Stemphone E3 Substance (1) Property: red powder (2) Molecular formula: $C_{30}H_{40}O_8$
HRFAB-MS (m/z) [M+H]$^+$ Calculated value: 529.2723, Measured value: 529.2720

(3) Molecular weight: 528
FAB-MS (m/z) [M+H]$^+$ 529

(4) Ultraviolet absorption spectrum: UV spectrum measured in methanol solution. λmax (MeOH, ε): Absorption at 202 nm (15014), 272 nm (11478), 473 nm (2748)
(5) Infrared absorption spectrum: IR spectrum measured by KBr tablet. Characteristic absorption maximum: vmax at 3434, 2927, 1733, 1648, 1621 cm$^{-1}$, etc.
(6) Specific rotation: $[\alpha]_D^{26}$ +7.12° (c=0.1, methanol)
(7) Solubility in solvent: Soluble in methanol and chloroform, and insoluble in water.
(8) Proton and carbon nuclear magnetic resonance spectra:
Chemical shift of hydrogen (ppm) and that of carbon (ppm) measured in deuterated chloroform by using Varian 300 MHz NMR spectrometer are as shown hereinbelow.

$\delta_H$: 0.98 (3H), 1.08 (3H), 1.10 (3H), 1.15 (3H), 1.47 (3H), 1.52 (3H), 1.56 (3H), 1.64-1.86 (3H), 1.87 (3H), 1.90-2.03 (2H), 2.20 (1H), 3.27 (1H), 3.55 (1H), 3.77 (1H), 4.22 (1H), 5.10 (1H), 5.49 (1H), 6.34 (1H), 6.42 (1H) ppm $\delta_c$: 11.5, 13.2, 17.1, 20.8, 21.1, 23.9, 24.0, 26.3, 26.6, 28.2, 34.1, 36.7, 44.8, 69.1, 71.8, 73.8, 77.2, 78.9, 81.0, 81.5, 111.5, 117.0, 125.3, 131.6, 131.8, 143.5, 149.0, 149.3, 170.0, 180.8, 184.6 ppm As explained hereinabove, as a result of detailed examination on various physico-chemical properties and spectral data of stemphone E3, stemphone E3 substance was determined to have chemical structure represented by the formula [V].

Stemphone F Substance
(1) Property: yellow powder
(2) Molecular formula: $C_{33}H_{48}O_{10}$
HRFAB-MS (m/z) [M+Na]$^+$ Calculated value: 627.3146, Measured value: 627.3151
(3) Molecular weight: 604
FAB-MS (m/z) [M+H]$^+$ 605
(4) Ultraviolet absorption spectrum: UV spectrum measured in methanol solution. λmax (MeOH, ε): Absorption at 201 nm (11669), 244 nm (6427), 288 nm (3603), 361 nm (387)
(5) Infrared absorption spectrum: IR spectrum measured by KBr tablet. Characteristic absorption maximum: vmax at 3438, 2967, 1658, 1629, 1623 cm$^{-1}$, etc.
(6) Specific rotation: $[\alpha]_D^{26}$ +148.9° (c=0.1, methanol)
(7) Solubility in solvent: Soluble in methanol and chloroform, and insoluble in water.
(8) Proton and carbon nuclear magnetic resonance spectra:
Chemical shift of hydrogen (ppm) and that of carbon (ppm) measured in deuterated chloroform by using Varian 300 MHz NMR spectrometer are as shown hereinbelow.

$\delta_H$: 0.95 (3H), 0.99 (3H), 1.13 (3H), 1.18 (3H), 1.28 (3H), 1.58-1.60 (3H), 1.61 (3H), 1.63 (3H), 1.82 (1H), 1.94-1.96 (2H), 1.94 (3H), 2.06 (1H), 2.30 (3H), 2.50 (1H), 2.94 (1H), 3.00 (1H), 3.56 (1H), 3.66 (1H), 4.11 (1H), 4.79 (1H), 5.14 (1H), 5.70 (1H), 6.06 (1H) ppm $\delta_c$: 11.1, 13.3, 13.4, 20.1, 21.5, 21.8, 23.8, 25.2, 26.5, 28.4, 33.5, 36.2, 37.4, 40.9, 46.4, 46.6, 62.4, 70.9, 71.9, 72.1, 76.7, 80.0, 83.1, 83.5, 110.1, 124.1, 127.5, 131.5, 162.0, 169.1, 169.4, 187.5, 209.9 ppm As explained hereinabove, as a result of detailed examination on various physico-chemical properties and spectral data of stemphone F, stemphone F substance was determined to have chemical structure represented by the formula [VI].

Biological properties of compound of stemphones of the present invention are described in detail as follows. Method for evaluation of enhancing effect for activity of imipenem by paper disk method Clinically isolated strain of methicillin resistant *Staphylococcus aureus* K24 was used as a test organism. *Staphylococcus aureus* was cultured in Mueller-Hinton broth (2.1% w/v) (DIFCO) at 37° C. for 20 hours, and was suspended corresponding to 0.5 Mc $F_{ARLAND}$ (about $10^8$ CFU/ml) in the same medium. The suspension was smeared on MHA medium (Mueller-Hinton broth 2.1% (w/v), agar 1.5%) and MHA medium added with imipenem (Banyu Seiyaku K.K., tienam for intramuscular injection, potency 0.5) to give a concentration for not to affect growth of the test organism, i.e. final concentration 10 µg/ml.

Smearing was performed by using sterilized cotton swab (Kawamoto Sangyo K.K., Japan) according to a method of National Committee for Laboratory Standard, NCCLS, U.S.A. Antibacterial activities against test organism on various media were expressed with a unit in mm of a diameter of inhibition zone after incubation with the paper disc (thin disc, 6 m, ADVANTEC Inc.) method at 37° C. for 20 hours. As a result, under the condition of 10 µg disc, the inhibitory zones were not observed by stemphone D substance, stemphone E substance, stemphone E1 substance, stemphone E2 substance, stemphone E3 substance and stemphone F substance, alone, whereas the inhibitory zones of 25 mm, 22 mm, 15 mm, 22 mm, 20 mm and 20 mm, respectively, were observed in the presence of imipenem. Since the inhibitory zone could not be observed by stemphone B substance and stemphone C substance alone, which were previously reported by the present inventors, whereas the inhibitory zone of 20 mm and 22 mm, respectively was observed in the presence of imipenem, it was obvious that newly isolated above substances had almost equal or more enhancing activity for imipenem.

Method for Evaluation of Cytotoxicity

Evaluation of cytotoxicity on Jurkat cells were performed by MTT method (Mosmaan, et al. J. Immunol. Methods, 65: 55-63, 1983). Cultured liquid of Jurkat cells were suspended in RPMI-1640 medium (Iwaki & Co., Ltd., Japan) to give suspension with $4 \times 10^5$ cells/ml, and the suspension 0.05 ml was seeded in each well of 96 well microplate (Corning Corp.). Subsequently, stemphone D substance, stemphone E substance, stemphone E1 substance, stemphone E2 substance, stemphone E3 substance or stemphone F substance (0.05 ml, 2% methanol/PRMI-1640 medium) was added and incubated at 37° C. for 48 hours in 5% carbon dioxide gas incubator. Then MTT reagent (SIGMA Inc.) dissolved in PBS to give concentration 5.5 mg/ml, 0.01 ml was added and reacted at 37° C. for 4 hours. After the reaction was performed, cell-lysing solution (40%, N-dimethylformamide (Kanto Chemical Co., Inc., Japan), 20% sodiumdodecyl sulfate (Wako Pure Chemical Industries, Ltd., Japan) 2% acetic acid (Kanto Chemical Co., Inc., Japan), 0.03% hydrochloric acid (Kanto Chemical Co., Inc., Japan) in purified water) 0.09 ml was added, and stirred at room temperature for 2 hours, then absorption at 550 nm was measured by using ELx 808 (BIO-TEK Instruments Inc.). $IC_{50}$ value for Jurkat cells are shown in the following Table. As compared with stemphone C substance previously reported by the present inventor (ratio: 1.0), about 4-fold to 60-fold reduction of toxicity were confirmed.

Result of cytotoxic test of compounds of stemphones

|  | IC50: µg/ml | Ratio |
| --- | --- | --- |
| Stemphone C substance | 0.4 | 1.0 |
| Stemphone D substance[I] | 1.8 | 4.2 |
| Stemphone E substance[II] | 3.6 | 8.5 |
| Stemphone E1 substance[III] | 26.2 | 60.9 |
| Stemphone E2 substance[IV] | 4.4 | 10.3 |
| Stemphone E3 substance[V] | 2.6 | 6.0 |
| Stemphone F substance[VI] | 2.7 | 6.3 |

BEST MODE FOR CARRYING OUT THE INVENTION

The present invention is explained by mentioning example, but the present invention is not limited within the example,

EXAMPLE

FKI-2136 strain cultured on agar slant medium (glycerin 0.1% (Kanto Chemical Co., Inc., Japan), $KH_2PO_4$ 0.08% (Kanto Chemical Co., Inc., Japan), $K_2HPO_4$ 0.02% (Kanto Chemical Co., Inc., Japan), $MgSO_4.7H_2O$ 0.02% (Wako Pure Chemical Industries, Ltd., Japan), KCl 0.02% (Kanto Chemical Co., Inc., Japan), $NaNO_3$ 0.2% (Wako Pure Chemical Industries, Ltd., Japan), yeast extract 0.02% (Oriental Yeast Co., Ltd., Japan), and agar 1.5% (SHIMIZU SHOKUHIN KAISHA, LTD., Japan), adjusted to pH 6.0) was inoculated with each one loopful thereof in large test tube, to which 10 ml of seed culture medium (glucose 2% (Wako Pure Chemical Industries, Ltd., Japan), polypeptone 0.5% (Wako Pure Chemical Industries, Ltd., Japan), $MgSO_4.7H_2O$ 0.05% (Wako Pure Chemical Industries, Ltd., Japan), yeast extract 0.2% (Oriental Yeast Co., Ltd., Japan), $KH_2PO_4$ 0.1% (Kanto Chemical Co., Inc., Japan), and agar 0.1% (SHIMIZU SHOKUHIN KAISHA, LTD., Japan), adjusted to pH 6.0) was dispensed and cultured at 27° C. for 2 days on the rotary shaker (300 rpm). The seed cultured strain was inoculated into the 500 ml Erlenmeyer flask (50 flasks) dispensed with 100 ml of the production medium (glucose 1.0% (Wako Pure Chemical Industries, Ltd., Japan), soluble starch (Kanto Chemical Co., Inc., Japan), soybean oil 2.0% (Wako Pure Chemical Industries, Ltd., Japan), pharma media 1.0% (Iwaki & Co., Ltd., Japan) meat extract 0.5% (KYOKUTO PHARMACEUTICAL INDUSTRIAL CO., LTD., Japan), $MgSO_4.7H_2O$ 0.1% (Wako Pure Chemical Industries, Ltd., Japan), $CaCO_3$ 0.3% (Kanto Chemical Co., Inc., Japan), trace salt solution 1.0% ($FeSO_4.7H_2O$ 0.1% (Kanto Chemical Co., Inc., Japan), $MnCl_2.4H_2O$ 0.1% (Kanto Chemical Co., Inc., Japan), $ZnSO_4.7H_2O$ 0.1% (Kanto Chemical Co., Inc, Japan), $CuSO_4.5H_2O$ 0.1% (Kanto Chemical Co., Inc., Japan), $CoCl_2.6H_2O$ 0.1% (Wako Pure Chemical Industries, Ltd., Japan), and agar 0.1% (SHIMIZU SHOKUHIN KAISHA, LTD., Japan), adjusted to pH 6.0), and cultured at 27° C., 210 rpm, for 7 days. Among them, one Erlenmeyer flask was further shake cultured at 27° C., 210 rpm, for 8 days.

After finishing the cultivation of the Erlenmeyer flask (49 flasks), the cultured fluid (4.9 lit.) was centrifuged to obtain supernatant and mycelia. Acetone (2.5 lit.) was added to the mycelia, stirred for 30 minutes and filtered the mycelia to obtain mycelial extract. Acetone was distilled off in vacuo from the mycelial extract to obtain aqueous residue which was combined with the supernatant, then active principle was extracted with ethyl acetate (5 lit.) from mixture of the aqueous residue and the supernatant, and the ethyl acetate layer was concentrated and dried in vacuo to obtain crude active substance (6.4 g). The crude substance was subjected to crude purification by silica gel column (silica gel 60, Merck, 60 g). Fractionation applying chromatography with developer solvent consisting of each mixed solvent of chloroform-methanol (100:0 (100 ml); 100:1 (200 ml), 50:1 (300 ml); 10:1 (300 ml); 5:1 (300 ml); and 1:1 (300 ml)) was performed.

At first, active fraction (50:1) was concentrated to dry to obtain brownish oily substance 704 mg. This crude substance was again purified by silica gel column (silica gel 60, Merck, 30 g). The chromatography with developer solvent consisting of each mixed solvent of chloroform-methanol (100:0 (50 ml×2); 100:1 (30 ml×5); 50:1 (25 ml×10); 10:1 (30 ml×5); and 5:1 (30 ml×5)) was performed for fractionation. Methanol soluble part 17 mg of the crude substance 30 mg obtained by concentrating and drying the active fractions (from 10:1 fraction No. 3 to 4) was purified by preparative HPLC (column: PEGASIL ODS, 20ϕ×250 mm, moving phase: 45% aqueous acetonitrile solution, flow rate: 6 ml/min., detection: UV 210 nm). A peak of retention time at 64 min. was collected and concentrated in vacuo to obtain stemphone D substance, yield 1.2 mg.

Further, active fractions after second silica gel column treatment (50:1 fraction No. 7-10) were concentrated and dried to obtain stemphone E substance, white powder, yield 318 mg. For synthesis of methylated stemphone E substance, stemphone E substance 50 mg was reacted with TMS-diazomethane 170 µl (Nacalai Tesque, Inc., Japan) in methanol 340 µl at 40° C. for 24 hours, then purified by preparative HPLC (column: PEGASIL ODS, 20ϕ×250 mm, moving phase: 70% aqueous acetonitrile solution, flow rate: 6 ml/min., detection: UV 210 nm). A peak of retention time at 22 min. was collected and concentrated in vacuo to obtain stemphone E1 substance, yield 11.6 mg. Further, for preparing dehydrated stemphone, after heating aqueous solution of stemphone E substance 50 mg to 60° C., concentrated and dried substance was dissolved in small amount of methanol, then the solution was purified by preparative HPLC (column: PEGASIL ODS, 20ϕ×250 mm). Isocratic solution of 70% aqueous acetonitrile solution was used as moving phase, and UV absorption at 210 nm was monitored in flow rate 6 ml/min. Peaks of retention time at 14 min. and 21 min. were collected, and the collected solution was concentrated in vacuo to obtain stemphone E2 substance and stemphone E3 substance, yield 12.0 mg and 2.3 mg, respectively.

After finishing the cultivation of the Erlenmeyer flask (one flask), the cultured fluid (0.1 lit.) was centrifuged to obtain supernatant and mycelia. Acetone (2.5 lit.) was added to the mycelia, stirred for 30 minutes and filtered the mycelia to obtain mycelial extract. Acetone was distilled off in vacuo from the mycelial extract to obtain aqueous residue which was combined with the supernatant, then active principle was extracted with ethyl acetate (0.5 lit.) from mixture of the aqueous residue and the supernatant, and the ethyl acetate layer was concentrated and dried in vacuo to obtain crude active substance (0.5 g). The crude substance was subjected to crude purification by silica gel column (silica gel 60, Merck, 2.3 g). Fractionation applying chromatography with developer solvent consisting of each mixed solvent of chloroform-methanol (100:0 (10 ml×4); 100:1 (10 ml×2); 50:1 (10 ml×3); 10:1 (10 ml×3); 5:1 (10 ml); and 1:1 (10 ml)) was performed. The crude substance 19.2 mg obtained by concentrating and drying the active fractions (from 50:1 fraction No. 2-3) was purified by preparative HPLC (column: PEGASIL ODS, 20ϕ×250 mm, moving phase: 50% aqueous acetonitrile solution, flow rate: 6 ml/min., detection: UV 210 nm). A peak of retention time at 18 min. was collected and concentrated in vacuo to obtain stemphone F substance, yield 10.3 mg.

INDUSTRIAL APPLICABILITY

Since each compound of stemphone D substance, stemphone E substance, stemphone E1 substance, stemphone E2 substance, stemphone E3 substance or stemphone F substance obtained from culture liquid by culturing microorganism represented by FKI-2136 strain belonging to genus *Aspergillus* having ability to produce novel compound of stemphones of the present invention has equal or more enhancing activity of imipenem as compared with previously reported stemphone C substance, and also has reducing cytotoxicity, it can be expected to be useful as lead compounds for combination remedy for methicillin resistant *Staphylococcus aureus* (MRSA) infection.

What is claimed is:
1. An isolated stemphone selected from the group consisting of:

stemphone D represented by the following formula [I]:

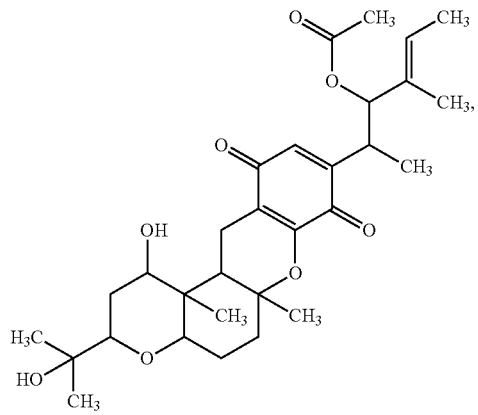

stemphone E represented by the following formula [II]:

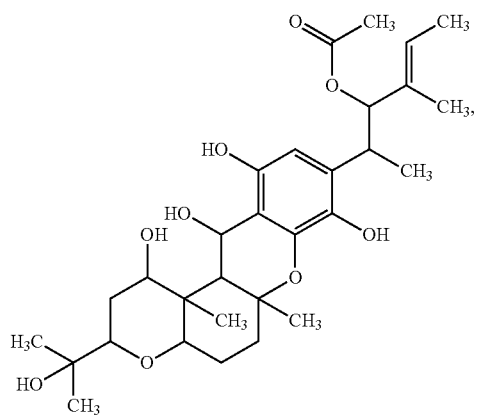

stemphone E1 represented by the following formula [III]:

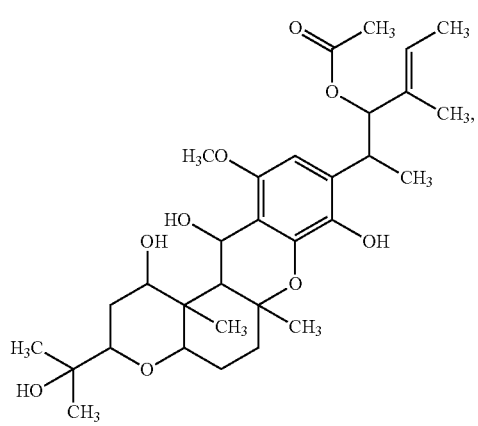

stemphone E2 represented by the following formula [IV]:

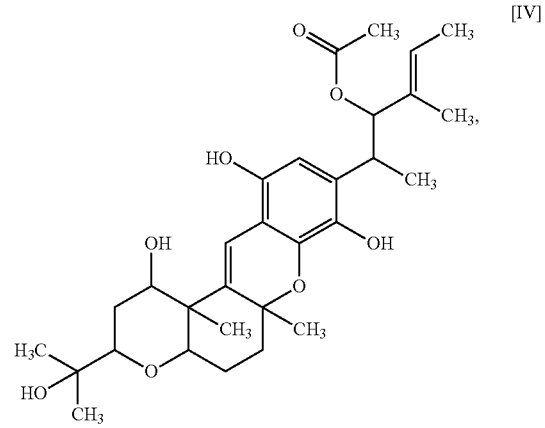

stemphone E3 represented by the following formula [V]:

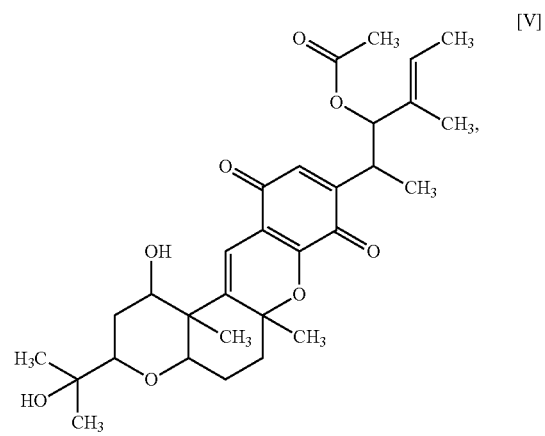

and
stemphone F represented by the following formula [VI]:

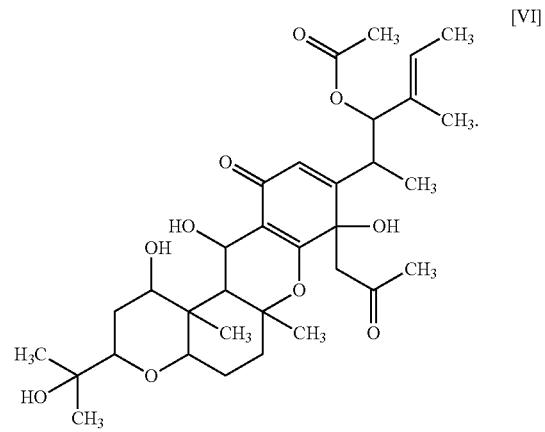

* * * * *